(12) United States Patent
Lai

(10) Patent No.: US 10,315,997 B2
(45) Date of Patent: Jun. 11, 2019

(54) CYCLOPROPYL UNSATURATED QUINOLINE COMPOUND USED AS LEUKOTRIENE RECEPTOR ANTAGONIST AND APPLICATIONS THEREOF

(71) Applicant: Guangdong Moltech Pharma Co., Ltd., Guangzhou (CN)

(72) Inventor: Yingjie Lai, Guangzhou (CN)

(73) Assignee: GUANGDONG MOLTECH PHARMA CO., LTD., Guangzhou (CN)

( * ) Notice: Subject to any disclaimer, the term of this patent is extended or adjusted under 35 U.S.C. 154(b) by 0 days.

(21) Appl. No.: 15/505,040

(22) PCT Filed: Sep. 10, 2015

(86) PCT No.: PCT/CN2015/089362
§ 371 (c)(1),
(2) Date: Feb. 17, 2017

(87) PCT Pub. No.: WO2016/197467
PCT Pub. Date: Dec. 15, 2016

(65) Prior Publication Data
US 2018/0118687 A1    May 3, 2018

(30) Foreign Application Priority Data
Jun. 10, 2015    (CN) .......................... 2015 1 0316361

(51) Int. Cl.
C07D 215/18    (2006.01)
A61K 31/47    (2006.01)
A61P 11/06    (2006.01)

(52) U.S. Cl.
CPC ............ C07D 215/18 (2013.01); A61K 31/47 (2013.01); A61P 11/06 (2018.01)

(58) Field of Classification Search
CPC .................................................. C07D 215/18
USPC .......................................... 546/174; 514/311
See application file for complete search history.

(56) References Cited

FOREIGN PATENT DOCUMENTS

| CN | 1061407 A | 5/1992 |
| CN | 1083052 A | 3/1994 |
| CN | 1139429 A | 1/1997 |
| CN | 102973532 A | 3/2013 |
| WO | 2007079252 A2 | 7/2007 |
| WO | 2008157658 A1 | 12/2008 |

OTHER PUBLICATIONS

Ivanisevic et al. "Use of X-ray . . . " Pharm. Sci. Encycl. p. 1-42 (2010).*
Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
Wolff, ed., Burger's Medicinal Chemistry and Drug Discovery, 5th edition, NY: John Wiley & Sons, 1996, vol. 1, pp. 949-976.*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory & Morris (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Jordan "Tamoxifen . . . " Nature Rev. v.2, p. 205-213 (2003).*
Ettnnayer et al. "Lessons Learned from Marketed and Investigational Prodrugs." J. Med. Chem., (2004), 47(10): 2393-2404.*

(Continued)

Primary Examiner — Patricia L Morris
(74) Attorney, Agent, or Firm — Vorys, Sater, Seymour and Pease LLP; Vincent M DeLuca

(57) ABSTRACT

A cyclopropyl unsaturated quinoline compound used as leukotriene receptor antagonist and applications thereof, wherein the structural formula of the compound is as follows:

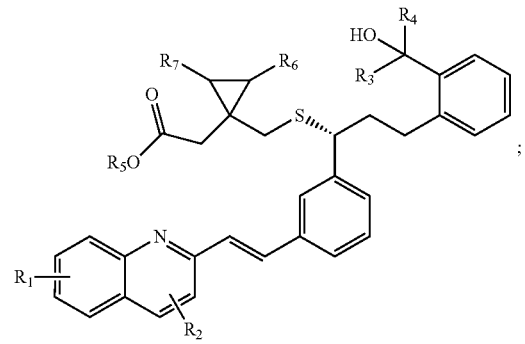

An application of the compound or its pharmaceutically acceptable salts, hydrates, solvates, or prodrugs in preparing a drug for treating and/or preventing and/or delaying and/or providing adjuvant therapy for asthma and/or allergic rhinitis and asthma syndromes is provided. A drug composition includes the cyclopropyl unsaturated quinoline compound or the pharmaceutically acceptable salts, hydrates, solvates, or prodrugs thereof. The compound series has favorable foreground in preparing the drugs for treating and/or preventing and/or delaying and/or providing adjuvant therapy for asthma and/or allergic rhinitis and asthma syndromes.

3 Claims, No Drawings

(56) References Cited

OTHER PUBLICATIONS

Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Bundgaard, Design of Prodrugs, Chapter 1, p. 1, 1985.*
Silverman, Prodrugs and Drug Delivery Systems, The Organic Chemistry of Drug Design and Drug Action, Chapter 8, pp. 352-400, 1992.*
Banker et al., Prodrugs, Modern Pharmaceutics, 3rd edition, Revised and Expanded, pp. 451 and 596, 1986.*
Saravanan, M., "Identification, synthesis, isolation and spectral characterization of potential impurities of montelukast sodium," Journal of Pharmaceutical and Biomedical Analysis, vol. 48, pp. 708-715, Jul. 16, 2008.

* cited by examiner

CYCLOPROPYL UNSATURATED QUINOLINE COMPOUND USED AS LEUKOTRIENE RECEPTOR ANTAGONIST AND APPLICATIONS THEREOF

TECHNICAL FIELD

The present invention relates to a cyclopropyl unsaturated quinoline compound used as leukotriene receptor antagonist and applications thereof.

BACKGROUND OF THE INVENTION

Asthma is a chronic inflammation disease characterized by reversible airway obstruction and non-specific bronchial hyperresponsiveness, and involves a complicated process of a series of inflammatory cells and inflammatory mediators. Common symptoms of an asthma patient are paroxysmal asthma, dyspnea, chest distress, or begma, and a few patients may have thoracodynia. At present, the asthma is a common disease and a frequently-occurring disease, which severely affects people's physical and psychological health.

The mechanism of airway obstruction in bronchial asthma (asthma) is related to bronchospasm caused by contraction of airway smooth muscle, mucous edema caused by vascular leakage, increased mucus secretion, and infiltration of inflammation cells induced by eosinophils, and a variety of inflammatory mediators, such as histamine, leukotrienes (LTs), thromboxane, prostaglandin, or the like, participate in an inflammation reaction of upper and lower airways. The asthma relates to a complicated process of a series of inflammatory cells and inflammatory meditors [British Medical Journal 1998, 316(15):1257-1258]. Researches show that leukotrienes plays an important role In the pathogenesisof asthma [Sampson A, Holgate S. Leukotriene modifiers in the treatment of asthma[J]. BMJ, 1998, 316(5): 1257-1258.], and plays an key role on the occurrence and development of the asthma. Therefore, the leukotriene receptor antagonist becomes the most effective mediator antagonist in clinic treatment of asthma, and uses of these drugs may accomplish an important breakout in asthma treatment.

In the later period of 1970s, cysteinyl leukotrienes (CysLT) is found to be an important mediator of asthma. The leukotrienes is generated by inflammatory cells such as mastocyte, oxyphil cell, or the like, and has multiple biological effects in the pathogenes is of asthma:increasing formation of vascular permeability and edema; increasing mucus production and reducing mucociliary transportation; attracting the inflammatory cells (such as eosinophils) to migrate from blood to the airway and release the inflammatory mediators, which may damage airway epithelium; and directly causing bronchospasm and stimulating the smooth muscle cell proliferation. The leukotrienes acts through the receptor thereof. The leukotriene receptors are distributed in all smooth muscle cells, dendritic cells, eosinophils, monocytes, macrophages, and B lymphocytes. An immunofluorescence detection shows that the CysLT1 receptors are distributed in both the smooth muscle of a central airway and a peripheral small airway in a lung tissue. The leukotriene receptor antagonist (LTRA) may improve aeration and relieve symptoms of asthma patient, which further proves the effect of the leukotrienes for asthma.

As gradually known effects of LTs in the bronchial hyperresponsiveness of asthma and confirmation of the LTs receptor sites, concerns have been raised about the situation the inhibitor sythesized by leukotriene receptor antagonist (LTRA) and LTs in prevention and treatment of asthma. The first leukotriene D4 (LTD4) receptor antagonist ibudilast (ibudilast, ketas) was applied in clinic in 1989. A new-generation LTRA zafirlukast (commercially named as encoreter) was marketed abroad as anti-asthmatic, anti-inflammatory and antiallergic drug in 1996, and had experienced certain clinic applications. Drugs with these LTs antagonism effects are a new trend to treat asthma at currently.

Mechanism of the leukotriene receptor antagonist (LTRAs) mainly lies in the following aspects: 1. Anti-inflammatory effect, preventing and relieving infiltration of inflammation cells. After taking zafirlukast or montelukast, as the improvement of lung function, lymphocyte counts, basophilic granulocyte counts, eosinophilic granulocyte counts, and scavenger cell counts in sputum, peripheral blood, and bronchoalveolar lavage fluid (BALF) of the patient are remarkablely reduced, and the reduction degree is related to the improvement degree of vital capacity and daytime symptoms; 2. Relaxing the bronchial smooth muscle; 3. Suppressing bronchus contraction caused by sports. In asthma patients, the bronchus contraction caused by sports is about 70% to 80%, and LTRAs can significantly suppress the bronchus contraction caused by sports; and 4. Effects on aspirin intolerance asthma (AIA), wherein the patient suffering from aspirin intolerance asthma present characteristics of chronic rhinitis, repeatedly occurrence of nasal polyp, asthma, and intolerance of the drugs like aspirin, and this asthma is difficult to control by regular treatments, and the patients of this type are often accompanied with over-producing cysteinyl leukotrienes and up regulation of LTC 4 synzyme. Many researches verify that the LTC4 synzyme of bronchus biopsy tissue of AIA is over expressed accompanying with increasing cysteinyl leukotriene level in the bronchoalveolar lavage fluid when comparing the patient suffering the aspirin intolerance asthma with healthy persons.

LTRAs has good tolerance, and large-scale clinical experiments in recent years verify that compared with a placebo, the LTRAs has significant clinical therapeutic effects, and no apparent side effect have been found in long term usage and has good tolerance, which is also very effective and safe for children, and no occurrence of death and severe negative reactions have been reported.

The LTRAs available on the market currently and applied in clinic mainly includes Zafirlukast (Zafirlukast, 安可来, Acolate), Pranukast (Pranukast), and Montelukast (Montelukast, 顺尔宁, Singulair). Wherein, Montelukast is a novel and powerful blocker drug of cysteinyl leukotriene receptor 1 (CysLTR.) with high selectivity and good tolerance developed in recent years, which can competitively antagonize the combination of leukotrienes D4 (LTD4) and Cys-LT1 receptor, thereby to suppress the activity of the leukotrienes, and reduce the expression of endothelium growth factor of blood vessel to adjust the permeability of the blood vessel, and improve the airway edema. The drug can effectively prevent and suppress the increase of vascular permeability, bronchospasm, and airway mucus hypersecretion caused by leukotrienes, and reduce the airway hyperresponsiveness, which has no apparent negative effects to important organs or systems, and has good compliance. As the inflammation mediator antagonist, its anti-asthmatic effect has been proved [Markham A, Faulds D. Montelukast [J]. Drugs, 1998, 56(2):251-7.]. The Montelukast is mainly used for prevention and long-term treatment of asthma of adult and child in clinic [LEE K S, KIM S R, PARK H S, et al. Cysteinyl leukotriene receptor antagonist regulates vascular permeability by reducing vascular endothelial growth factor expression[J]. Allergy Clin Immunol, 2004, 114(5): 1093-1099.]. A double-blind, random, crossed and antithetical clinical research shows that the Montelukast can significantly suppress bronchus contraction caused by inhaling LTD4 [De Lepeleire I, Reiss T F, Rochette F, et al. Montelukast causes prolonged, potent leukotriene D4-receptor antagonism in the airways of patients with asthma [J]. Clin Pharmacol Ther, 1997, 61(1): 83.]. The Montelukast may also suppress the bronchus contraction caused by movement, Bronsky E A, et al. [Bronsky E A, Kemp J P, Zhang J, et al". Dose related protection of exercise bronchoconstriction by montelukast, a cysteinyl leukotriene-receptor antagonist, at the end of a once-daily dosing interval [J]. Clin Pharmacol Ther, 1997, 62(5):556.]. The suppression condition of the Montelukast to the bronchus contraction caused by sports is tested on the asthma patient.

Montelukast sodium (Singulair) is the first oral leukotriene receptor antagonist. The leukotriene is one of the important mediators in a series of inflammatory cells and inflammatory mediators in pothogenesy of the bronchial asthma, and plays a key role in generation and development of the bronchial asthma in the pathophysiology of the asthma.

Montelukast sodium (Montelukast, Singulair) is one unique high-selectivity leukotriene receptor antagonist intaken once a day currently, and is suitable for treating asthma of adult and child, and syndrome of asthma and anaphylactic rhinitis asthma. Since the Montelukast has a relatively wide application range, and is convenient to intake, it has been widely recognized by clinician and used in clinic currently although manufacturing and application in clinic very late.

Recently, Adverse Events Reporting System (AERS) of Food and Drug Administration (FDA) has received many reports about side effects on neuropsychiatric aspect of anti-leukotriene drugs relating to the Montelukast (Singulair) or the like, and most reports are related to the Montelukast (Singulair) that may induce a suicide tendency. The drug is the most frequently-used anti-leukotriene prescription drug currently, and from clinical description of the suicide reports of some patients, the negative suicide events are actually caused by the drugs. Food and Drug Administration (FDA) sent an announce to medical workers and patients on Mar. 27, 2008 [Announcement Mar. 27, 2008], and considered that the use of the Singulair may possible to cause changes of behavior/emotion and suicide tendency and behavior. The patient transitorily does not need withdrawal, but clinical doctors should closely monitor whether the patients taking these drugs present changes of behavior/emotion, and whether the patients develop suicide tendency and behavior. For the children taking Montelukast (Singulair), it should be pay attention to these children whether present appearances of hyperactivity, attention deficit, aggressive behavior, lethargy, depression, etc.

In 2009, after investigations, FDA officially informed that three asthma drugs including Montelukast (Singulair) have a possibility to cause mental-health problems, and manufacturers of anti-leukotriene drugs should mark drug-induced risks on drug label. FDA issued a declaration on its website to indicate that some asthma patients taking Montelukast (Singulair), Accolte, and Zileuton appear side effects of depressive illness, anxiety, suicide tendency, etc. This FDA investigation verifies that three asthma drugs including Montelukast (Singulair) have a possibility to cause mental-health problems. FDA stated that both clinical doctors and asthma patients should clearly know potential risks of these drugs to the mental health.

A spokesman from Merck Corporation which is a manufacturer of Montelukast (Singulair) stated that the risk of neuropsychiatric side effects has been noted in the "negative reaction" part of the instructions of Montelukast (Singulair), and it will be described in the part of matters needing attention of the drug in future.

The prior art has described some quinoline-containing compounds served as antagonist and having active effects to leukotrienes.

For example, EP318,093 (Merck) and CN1061407A (Merck Frosst Canada Inc.) describe a compound having structure A. A compound having a structural formula B has been disclosed in WO89/12629 (Rorer) and US005565473A.

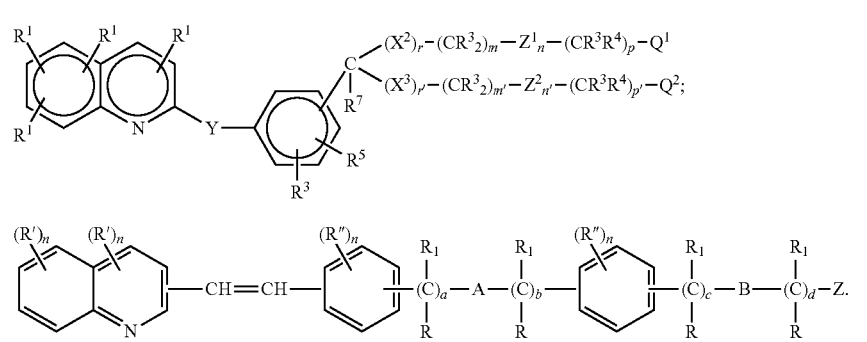

SUMMARY OF THE INVENTION

One object of the present invention is to provide a cyclopropyl unsaturated quinoline compound used as leukotriene receptor antagonist and applications thereof.

The invention employs the following technical solutions:

A cyclopropyl unsaturated quinoline compound or its pharmaceutically acceptable salts, hydrates, solvates, or prodrugs used as leukotriene receptor antagonist has a structural formula shown below:

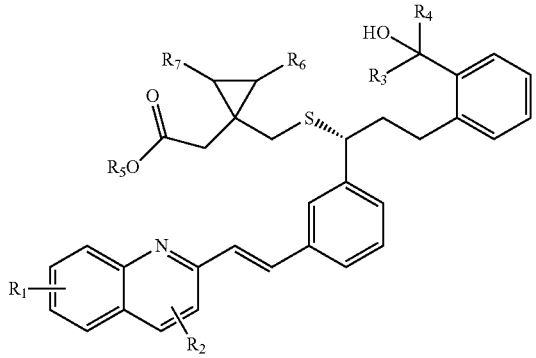

wherein:

$R^1$ and $R^2$ represent H, halogen, —$CF_3$, —CN, —$NO_2$, or $N_3$;

$R^3$ represents lower alkyl, lower alkenyl, —$CF_3$, —$CH_2F$, —$CHF_2$, $CH_2CF_3$, substituted or unsubstituted phenyl, substituted or unsubstituted benzyl, substituted or unsubstituted 2-phenethyl or a ring of up to 8-members containing 0 to 2 heteroatoms formed with two $R^2$ groups connected to one and the same carbon atom, wherein the heteroatoms are selected from O, S and N;

$R^4$ represents H or $R^3$;

$R^5$ represents H or a cation corresponding to a pharmaceutically acceptable salt;

$R^6$ and $R^7$ represent H, halogen, —$CF_3$, —CN, —$NO_2$, or $N_3$.

The lower alkyl is C1-8 alkyl, and the lower alkenyl is C1-8 alkenyl.

A cyclopropyl unsaturated quinoline compound or its pharmaceutically acceptable salts, hydrates, solvates, or prodrugs used as leukotriene receptor antagonist has a structural formula shown below:

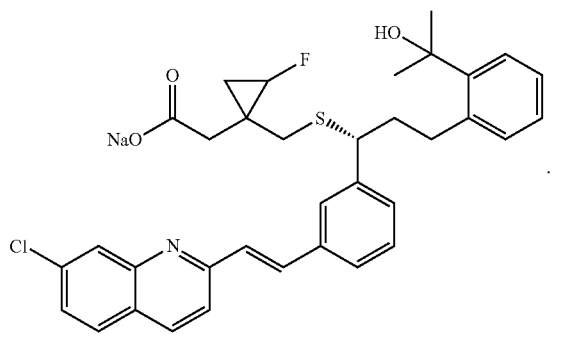

A cyclopropyl unsaturated quinoline compound or its pharmaceutically acceptable salts, hydrates, solvates, or prodrugs used as leukotriene receptor antagonist has a structural formula shown below:

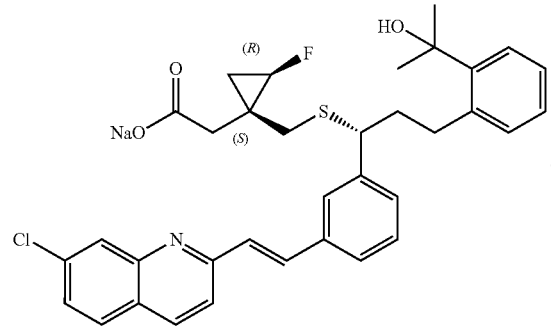

A cyclopropyl unsaturated quinoline compound or its pharmaceutically acceptable salts, hydrates, solvates, or prodrugs used as leukotriene receptor antagonist has a structural formula shown below:

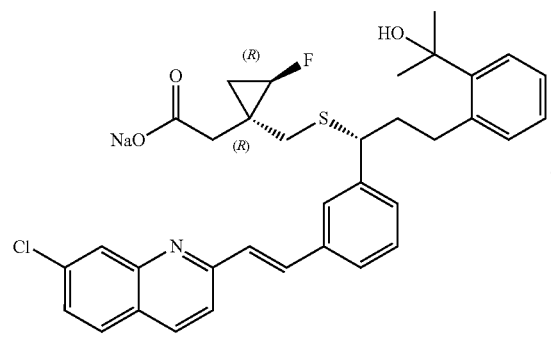

A cyclopropyl unsaturated quinoline compound or its pharmaceutically acceptable salts, hydrates, solvates, or prodrugs used as leukotriene receptor antagonist has a structural formula shown below:

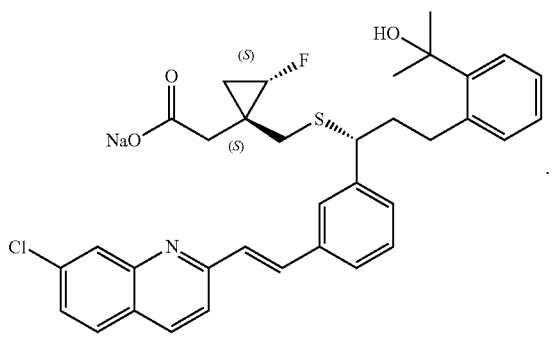

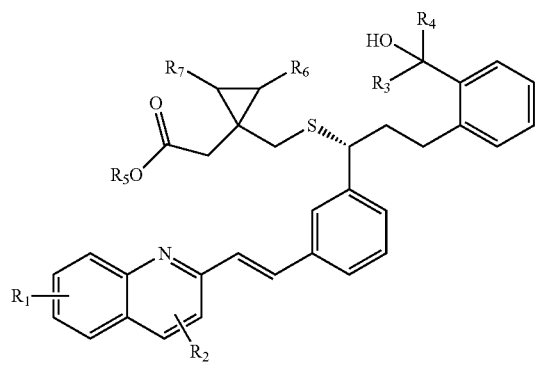

An application of the cyclopropyl unsaturated quinoline compound or its pharmaceutically acceptable salts, hydrates, solvates, or prodrugs used as leukotriene receptor antagonist in preparing a drug for treating and/or preventing and/or delaying and/or providing adjuvant therapy for asthma and/or allergic rhinitis and asthma syndromes.

A drug composition includes the above cyclopropyl unsaturated quinoline compound or its pharmaceutically acceptable salts, hydrates, solvates, or prodrugs used as leukotriene receptor antagonist.

The above drug composition further includes other pharmaceutically excipients.

The beneficial effects of the present invention are as follows:

The series compound of the present invention has favorable foreground in preparing the drugs for treating and/or preventing and/or delaying and/or providing adjuvant therapy for asthma and/or allergic rhinitis and asthma syndromes.

Specifically, acute toxicity tests in KM mice shows that a series of cyclopropyl unsaturated quinoline compound prepared according to the present invention is relatively safe, reliable and innoxious in a therapeutic dosage range.

In-vivo anti-asthmatic pharmacodynamics tests results shows that an isomeric compound particularly has a favorable anti-asthmatic effect on asthma guinea pig models and has more significant effects than the montelukast control group with the same dosage, which is a very promising candidate lead compound for developing highly-effective and low-toxicity anti-asthmatic drugs.

The series compounds of the present invention has favorable foreground in preparing drugs for treating and/or preventing and/or delaying and/or providing adjuvant therapy for asthma and/or allergic rhinitis and asthma syndromes.

DETAILED DESCRIPTION OF THE INVENTION

A cyclopropyl unsaturated quinoline compound or its pharmaceutically acceptable salts, hydrates, solvates, or prodrugs used as leukotriene receptor antagonist has a structural formula shown below:

Preferably, $R^1$ and $R^2$ represent H, halogen, —$CF_3$, —CN, —$NO_2$, or $N_3$;

$R^3$ represents lower alkyl, lower alkenyl, —$CF_3$, —$CH_2F$, —$CHF_2$, $CH_2CF_3$, substituted or unsubstituted phenyl, substituted or unsubstituted benzyl, substituted or unsubstituted 2-phenethyl or a ring of up to 8-members containing 0 to 2 heteroatoms formed with two $R^2$ groups connected to one and the same carbon atom, wherein the heteroatoms are selected from O, S and N;

$R^4$ represents H or $R^1$;

$R^5$ represents H or a cation corresponding to a pharmaceutically acceptable salt; and $R^6$ and $R^7$ represent H, halogen, —$CF_3$, —CN, —$NO_2$, or $N_3$.

Further preferably, the lower alkyl is a C1-8 alkyl, and the lower alkenyl is a C1-8 alkenyl.

In the above compounds, the acid groups may form salts with bases, and examples of forming salts with bases include but are not limited to: forming salts with inorganic alkali metal hydroxides, alkali metal carbonates, alkali metal bicarbonates, alkaline earth metal hydroxides, alkaline earth metal carbonates, or alkaline earth metal bicarbonates; and forming salts with organic bases such as procaine, and forming salts with basic amino acids such as lysine.

Preferably, the cyclopropyl unsaturated quinoline compound or its pharmaceutically acceptable salts, hydrates, solvates, or prodrugs used as leukotriene receptor antagonist is at least one of the following compounds:

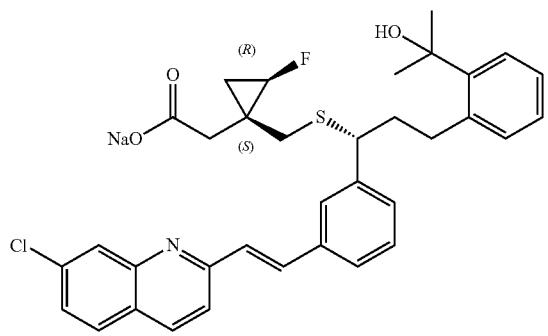

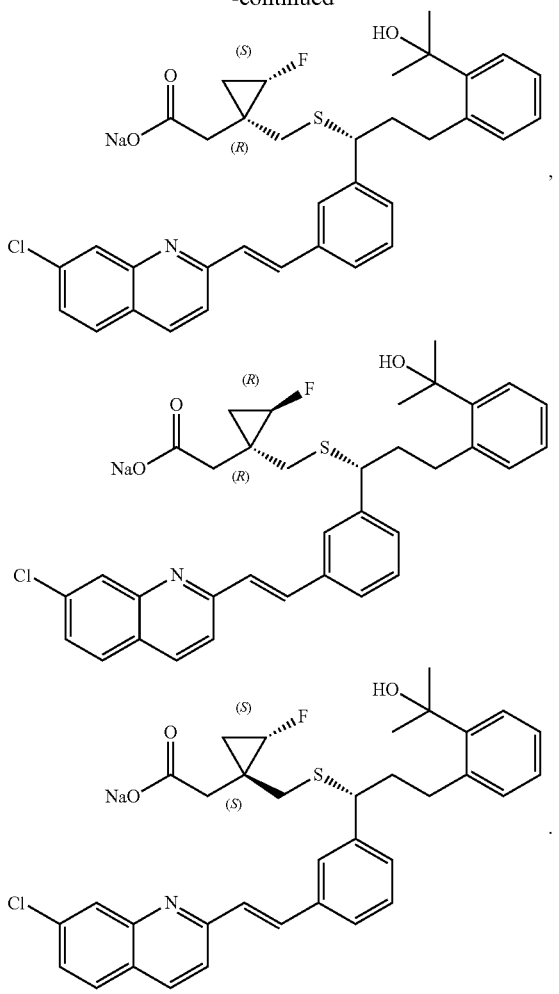

In the above compounds, basic groups may form salts with acids, and examples of forming salts with acids include but are not limited to: forming salts with inorganic acids, especially with haloid acids (e.g. hydrochloric acid, hydrobromic acid, and hydroiodic acid), nitric acid, sulfuric acid, phosphoric acid, carbonic acid and the like; forming salts with lower alkyl sulfonic acids such as methane sulfonic acid and trifluoromethane sulfonic acid; forming salts with aryl sulphonic acids such as benzenesulfonic acid or p-toluenesulfonic acid; forming salts with organic acids such as an acetic acid, fumaric acid, tartaric acid, oxalic acid, citric acid, maleic acid, malic acid or succinic acid; and forming salts with amino acids such as aspartic acid or glutamic acid.

Application of the cyclopropyl unsaturated quinoline compound or pharmaceutically acceptable salts, hydrates, solvates, or prodrugs used as leukotriene receptor antagonist in preparing drugs for treating and/or preventing and/or delaying and/or providing adjuvant therapy for asthma and/or allergic rhinitis and asthma syndromes.

A drug composition includes the above cyclopropyl unsaturated quinoline compounds or pharmaceutically acceptable salts, hydrates, solvates, or prodrugs used as leukotriene receptor antagonist.

The above drug composition further includes pharmaceutically excipients.

Preferably, the excipient includes at least one of the following: solvents, propellants, solubilizers, stabilizers, glidants, corrigents, preservatives, suspending agents, coating materials, aromatics, antiadherents, chelating agents, penetration enhancers, pH adjusters, buffers, plasticizers, cosolvents, emulsifiers, colorants, adhesives, disintegrating agents, filler, lubricants, wetting agents, osmolarity regulators, surfactants, foaming agents, defoaming agents, thickeners, inclusion agents, humectants, absorbents, diluents, flocculents and anticoagulants, filter aids, and releasing retardents.

The drug composition of the present invention may be prepared into various dosage forms: classifying according to the dispersion system of the dosage form, which may specifically be formulated into the following dosage forms including solution forms, colloidal solution forms, emulsion forms, suspension forms, gas dispersion forms, particle dispersion forms and solid dispersion forms; classifying according to physical state of materials, which may specifically be formulated into the following dosage forms including liquid forms (such as aromatic water, solution, injection, mixture, lotion, liniment, etc), gas forms (such as aerosol, spray, etc), solid forms (such as powder, pill, tablet, membrane, etc), and semi-solid forms (such as ointment, suppositories, paste, etc); and classifying according to administration route, which may specifically be formulated into the following forms including dosage forms for gastrointestinal tract administration, and dosage forms for parenteral administration.

A synthetic route of the compound according to the present invention is as follows:

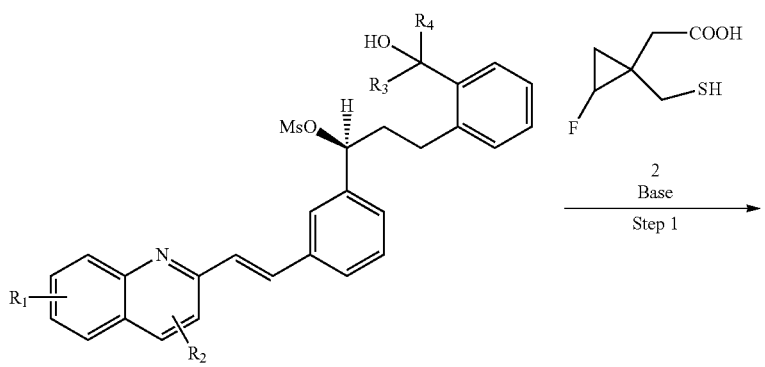

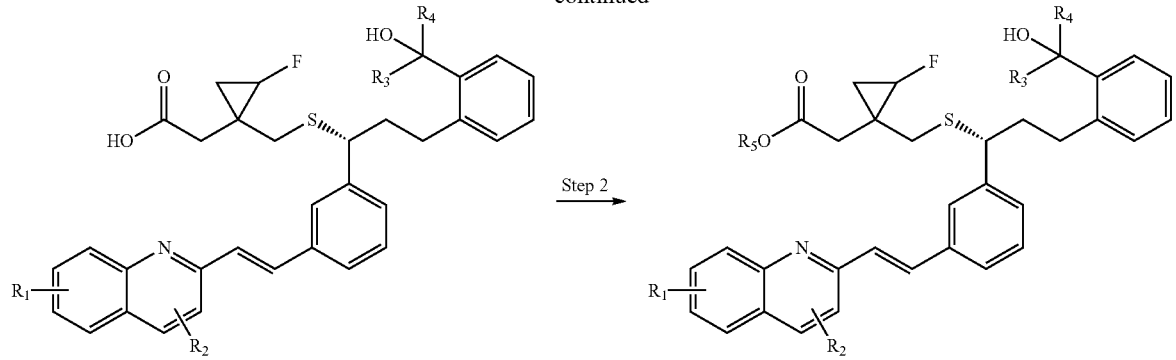

3

$R_1 = Cl, R_2 = H, R_3 = H, R_4 = CH_3, R_5 = Na^+$

4

The present invention will be further described hereinafter with reference to the preferred embodiments.

Example 1: Synthesis of Fragment Compound 2

Synthetic Scheme:

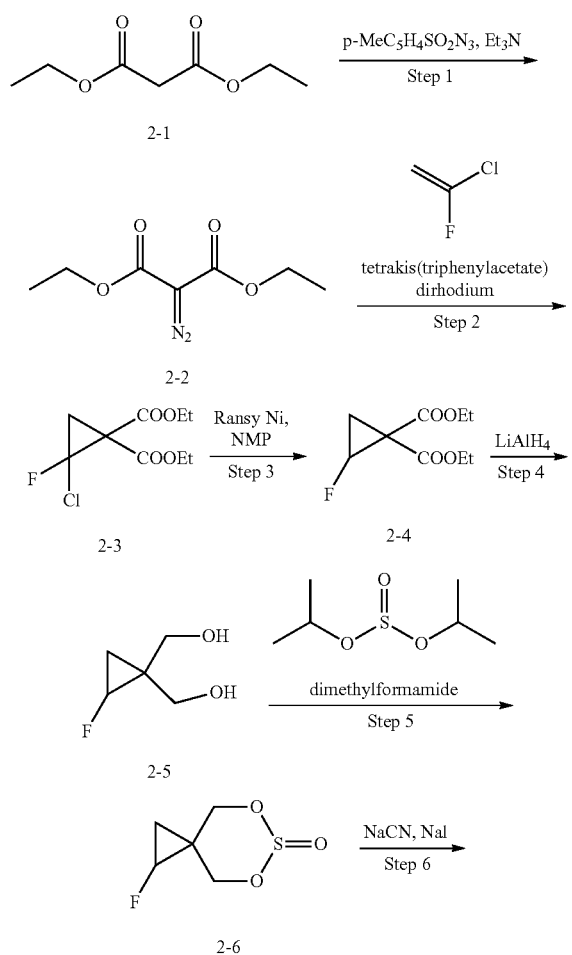

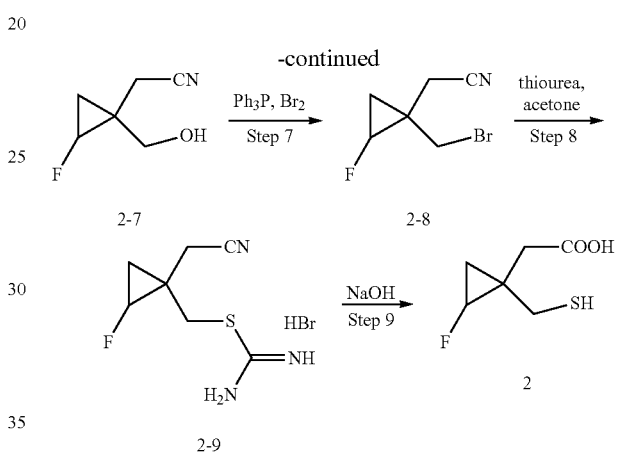

(1) Synthesis of Compound 2-2

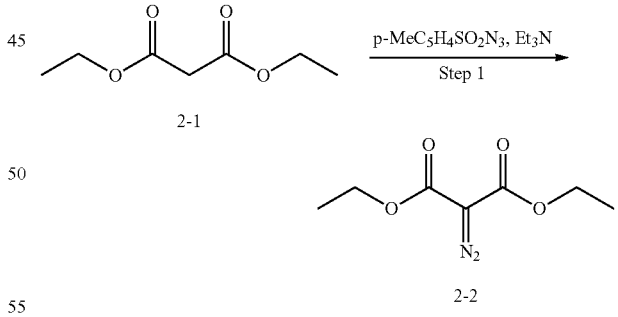

At 0 to 5° C., a triethylamine (104 mmol) and a p-toluenesulfonyl azide (20.5 g, 104 mmol) solution in acetonitrile (100 mL) were sequentially added into a diethyl malonate (87 mmol) solution in acetonitrile (150 mL). After the addition was completed, the mixture was stirred at room temperature overnight. When the reaction was finished, the reaction solution was concentrated under reduced pressure, and then was added with 100 mL ethyl ether. The organic layer was sequentially washed by 1N aqueous sodium hydroxide (50 mL), water (50 mL) and saturated brine (50 mL), dried by anhydrous sodium sulfate, and then was concentrated under reduced pressure to obtain 17 g compound 2-2 (yield: 100%).

$^1$H NMR (CDCl$_3$ 400 MHz): δ4.30-4.25 (q, J=6, 4H), δ 1.31-1.27 (t, J=6, 6H).

(2) Synthesis of Compound 2-3

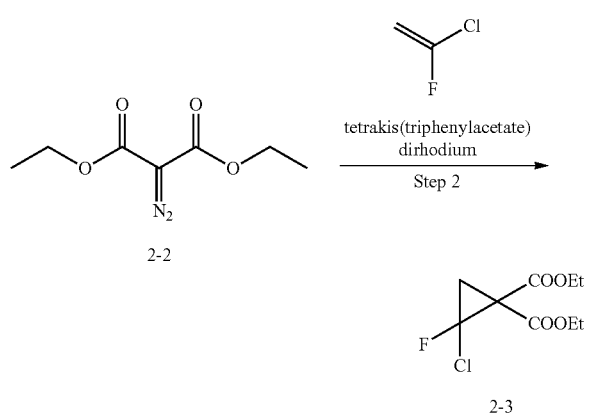

At −60° C., 1-chloro-1-vinyl fluoride (14.9 mol) was added into a methylene chloride (20 L) suspension of Tetrakis(triphenylacetato)dirhodium(II) (48 g) and powder molecular sieve (720 g), then the reaction solution was warmed up to −35° to −40° C., and was added with the solution of the compound 2-2 (11.47 mol) in methylene chloride (4 L). After the addition was completed, the reaction mixture was stirred at room temperature overnight. The reaction solution was filtered, and the filtrate was concentrated to obtain 2.9 Kg yellow oily crude compound 2-3, which was directly used in next reaction without further purification.

(3) Synthesis of Compound 2-4

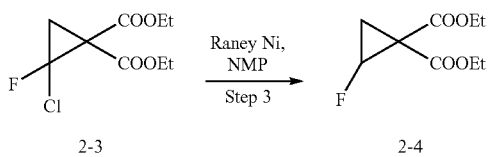 [SMILES: CCOC(=O)C1(C(=O)OCC)CC1(F)Cl ; CCOC(=O)C1(C(=O)OCC)CC1F]

At 80° C., raney nickel (380 g) and ethylenediamine (632 g) were added into the solution of crude compound 2-3 (3.35 mol) in N-methyl pyrrolidone (4.5 L), which was filled with hydrogen to react overnight. After the reaction was completed, the reaction solution was cooled to room temperature and was added with ethyl acetate (15 L), then it was filtered and the filtrate was sequentially washed by 2N aqueous hydrochloric acid solution and saturated brine, dried by anhydrous sodium sulfate and filtered, then the filtrate was concentrated under reduced pressure, and was purified through column chromatography to obtain 518 g compound 2-4 (yield: 65%).

$^1$H NMR (CDC$_3$ 400 MHz): δ 4.75-4.48 (m, 1H), δ 4.29-4.25 (q, J=6, 4H), δ 1.77-1.53 (m, 2H), δ 1.33-1.28 (t, J=6, 6H).

(4) Synthesis of Compound 2-5

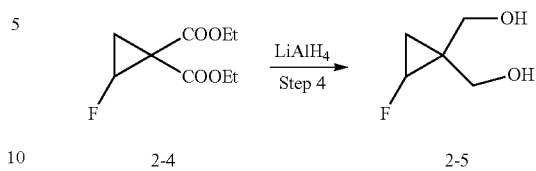

At 0° C., the solution of the compound 2-4 (10.7 mmol) in tetrahydrofuran (15 mL) was slowly added dropwise into the suspension of LiAlH$_4$ (35.4 mmol) in tetrahydrofuran (100 mL), and then the mixture was stirred at room temperature for 1 h. After completing the reaction, adding water to quench the reaction. The suspension was filtered through Celite, and the filtrate was concentrated under reduced pressure, and then purified through column chromatography to obtain 1 g compound 2-5 (yield: 78%).

$^1$H NMR (CDC$_3$ 400 MHz): δ 4.70-4.54 (m, 1H), δ 4.09-2.98 (m, 6H), δ 0.95-0.82 (m, 2H).

(5) Synthesis of Compound 2-6

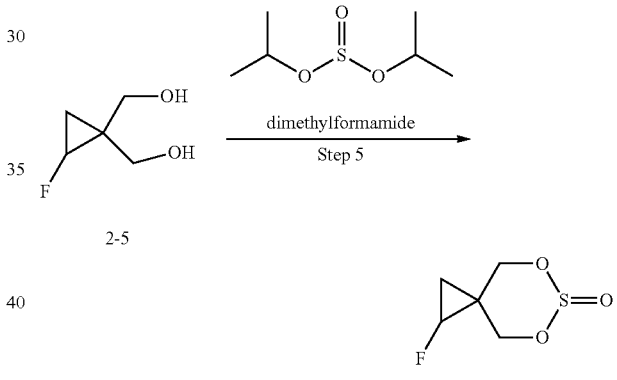

The solution of the compound 2-5 (250 mmol) in DMF (225 mL) was added into a 1 L reaction flask which was equipped with a vacuum distillation unit; when the reaction temperature reached 75° C./50 torr, 25 mL DMF was distilled out, then the solution (81.6 mL, 300 mmol) of isopropyl sulfite in toluol was added into the reaction solution, wherein 50 mL toluol could be collected at 52° C./55 torr. Then sodium tert-butoxide (2 M in THF, 2.0 mL) was added into the reaction solution, the mixture was distilled at 35°/50 torr and 30 mL fraction could be collected; the temperature was continuously raised up to 70° C./50 torr and the mixture was distilled, 60 mL fraction could be collected. After that sodium tert-butoxide (2 M in THF, 1.0 mL) was added, and the mixture was continuously distilled at 60-75° C./50 torr and 60 mL fraction could be collected. Then sodium tert-butoxide (2 M in THF, 0.5 mL) was added, and the mixture was continuously distilled at 70-75° C./50 torr, the distillation was stopped when 30 mL fraction was collected. The reaction solution was stirred at 70° C. for 1 h, then cooled to room temperature, and was processed to obtain a compound 2-6 solution.

(6) Synthesis of Compound 2-7

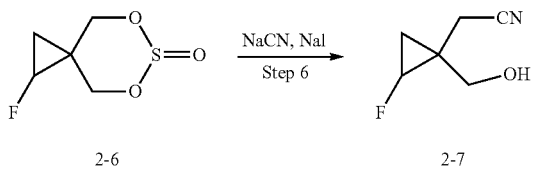 [SMILES: O=S1OCC2(CO1)CC2F ; N#CCC1(CO)CC1F]

Sodium cyanide (275 mmol) and sodium iodide (50 mmol) were added into the compound 2-6 solution above, which warmed up to 70° C. and stirred for 1 h, and then was stirred vigorously for 4 h; After that toluol (400 mL) was slowly added at 70° C., and then water (6 mL) was slowly added dropwise for 30 min. After the dropwise addition was completed, distillation under a reduced pressure was performed, and 100 mL toluol can be distilled out, then the reaction solution was cooled to 10° C. and filtered, the filter cake was rinsed with toluol (100 mL), and the filtrate was combined and concentrated and purified through column chromatography to obtain 24 g compound 2-7 (yield of the two steps: 74%).

$^1$H NMR (CDCl$_3$ 400 MHz): δ 4.67-4.48 (m, 1H), δ 3.88-3.33 (m, 2H), δ 2.76-2.34 (m, 2H), δ 1.11-0.91 (m, 2H).

(7) Synthesis of Compound 2-8

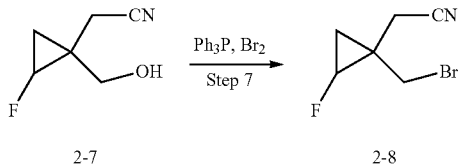

Triphenylphosphine (0.28 mol) was dissolved in 300 mL acetonitrile, cooled to −8° C., then was slowly added dropwise with bromine (0.27 mol), and the reaction solution was stirred at 5° C. until yellow color disappeared, then the solution of the compound 2-7 (0.27 mol) in acetonitrile was added dropwise and the temperature was kept below 10° C.; after the dropwise addition was completed, the reaction solution was heated to 60° C. and stirred for 15-20 min. Then the reaction solution was cooled to a temperature below −10% and kept for 1 h, and filtered; then the filter cake was rinsed with low temperature acetonitrile (2×100 mL), and the filtrate was combined and concentrated under reduced pressure, the concentrate was dissolved in methyl tertiary butyl ether (100 mL), and was stirred at −8° C. to 3° C. for more than 1 h followed by filtering, and the filter cake was rinsed with low temperature methyl tertiary butyl ether (2×100 mL), and the filtrate was combined and concentrated to obtain 45 g compound 2-8 (yield: 87%).

$^1$H NMR (CDCl$_3$ 400 MHz): δ 4.69-4.50 (m, 1H), δ 3.51-3.24 (m, 2H), δ 2.56-2.37 (m, 2H), δ 1.18-1.01 (m, 2H).

(8) Synthesis of Compound 2-9

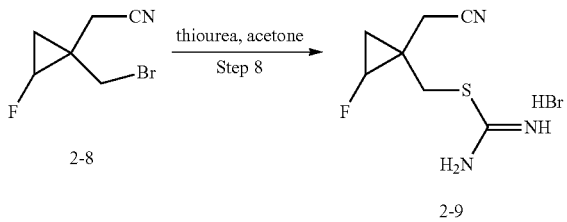 [SMILES: N#CCC1(CBr)CC1F ; N#CCC1(CSC(=N)N)CC1F ; Br]

The compound 2-8 (0.187 mol), acetone (165 mL) and thiourea (0.189 mol) were added into a 500 mL double-mouth bottle, the reaction solution was heated and reflowed for 12 h, then the reaction solution was cooled to −8° C. to 3° C., continuously stirred for more than 1 h, and filtered; the filter cake was rinsed with low temperature acetone (2×25 mL), then the filter cake was pulped for 5 h with 87 mL acetone, and filtered, then the filter cake was re-rinsed with low temperature acetone (2×25 mL), sucked dry, and dried under vacuum to obtain 44 g compound 2-9 (yield: 90%).

(9) Synthesis of Fragment Compound 2

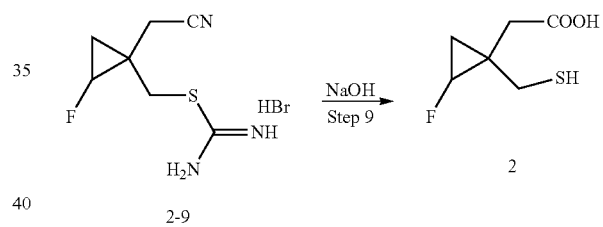

Under nitrogen protection, the compound 2-9 (0.04 mol) and 20% deaerated sodium hydroxide solution (38.3 mL) were added into a 100 mL three-mouth bottle, heated and reflowed for 14 h, and then cooled to room temperature, added with deaerated ethyl acetate, continuously cooled to −5 to 5° C., and then 85% formic acid was added to adjust the pH value to between 3.5 and 4.0. The organic phase was separated and the aqueous phase was continuously extracted with ethyl acetate, then the organic phase was combined and washed with water, dried by anhydrous sodium sulfate, and concentrated under reduced pressure to obtain a crude product, and the crude product was further crystallized byn-hexane to obtain 5 g fragment compound 2 (yield: 76%).

$^1$H NMR (CDCl$_3$ 400 MHz): δ 8.87 (br, 1H), δ 4.61-4.43 (m, 1H) δ 2.91-2.66 (m, 2H), δ 2.56-2.22 (m, 2H), δ 1.49-1.45 (m, 1H), 0.99-0.84 (m, 2H).

$^{13}$C NMR (CDCl$_3$ 500 MHz): δ 178, δ177, δ77, δ76; δ 36, δ 33, δ 29, δ 26, δ24, δ23; δ 18, δ 16.

$^{19}$F NMR (CDCl$_3$ 470 MHz): δ −214: δ −219.

Example 2 Synthesis of Compound 4
The synthesis scheme is as follows:
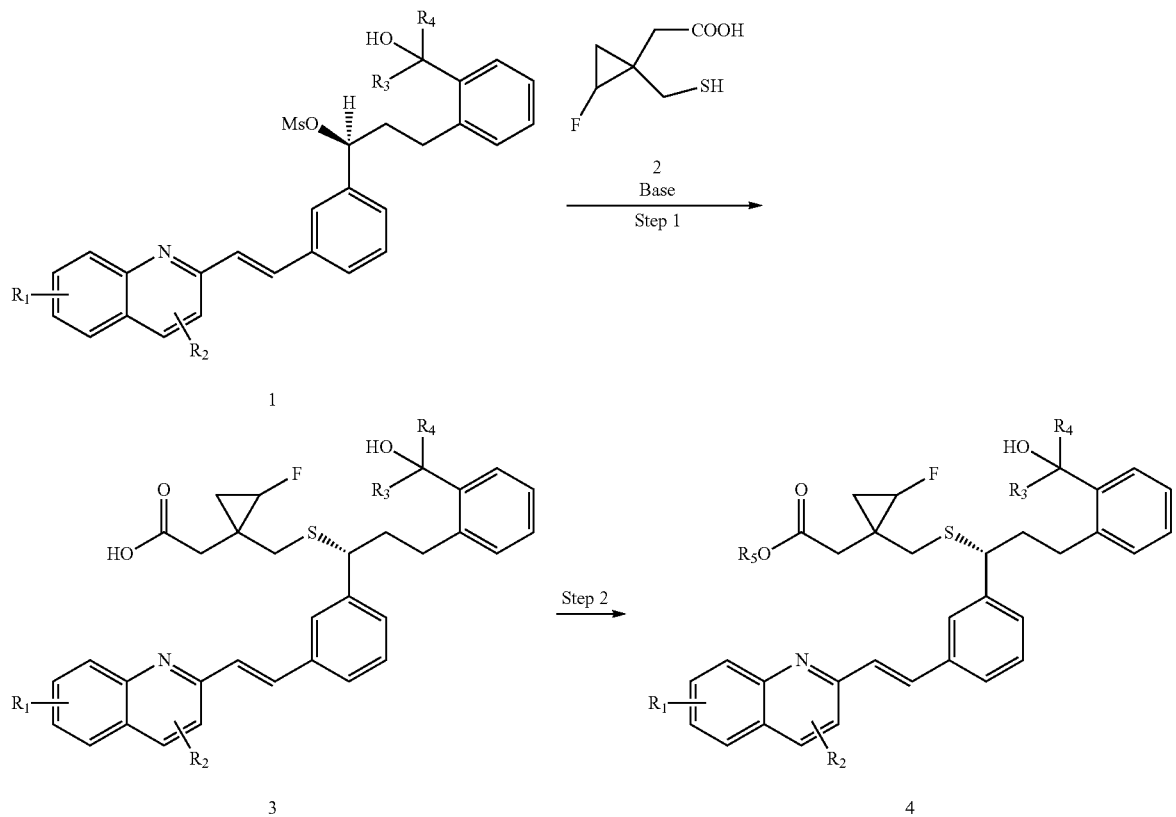
$R_1 = Cl, R_2 = H, R_3, R_4 = CH_3, R_5 = Na^+$
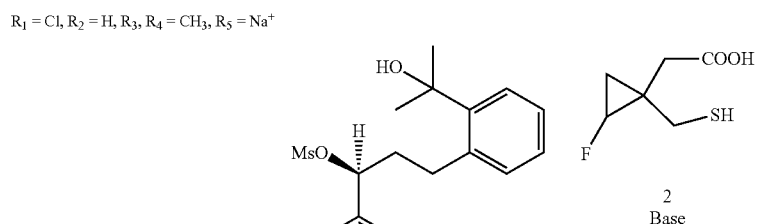
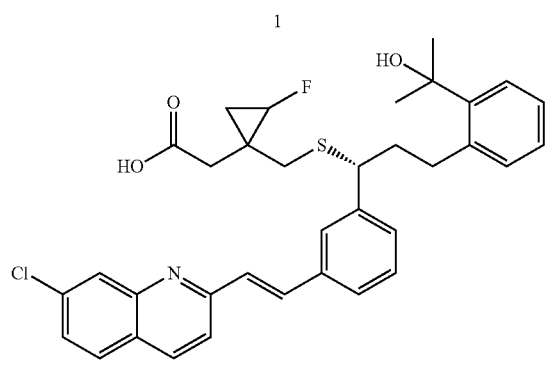

(1) Synthesis of Compound 3

(2-fluoro-cyclopropyl)-1-mercaptoethyl acetic acid (33 mmol), cesium carbonate (98 mmol) and polyethylene glycol-400 (10 g) were placed into a flask, added with DMF (50 mL), stirred for 1 h under room temperature. Then the reaction solution was cooled to −15° C., dropwise added with the solution of the compound 1 (33 mL) in THF (45 mL); after the dropwise addition was completed, the reaction solution was warmed up to room temperature and stirred for 8 h. 1 M hydrochloric solution (100 mL) was added, and the mixture was extracted by ethyl acetate (3×50 mL), then the organic phase was combined and washed with saturated brine, dried and concentrated to obtain a crude product, then the crude product was crystallized with ethyl acetate/petroleum ether to obtain 16 g yellow solid compound (yield: 80%).

$^1$H NMR (CDCl$_3$ 400 MHz): δ 8.09-8.06 (m, 2H), δ 7.75-7.48 (m, 4H), δ 7.45-7.31 (m, 6H), δ 7.16-7.11 (m, 3H), δ 5.20 (br, 1H), δ 4.61-4.36 (m, 1H), δ 4.01-3.98 (m, 1H), δ 3.23-3.02 (m, 1H), δ 2.94-2.51 (m, 4H), δ 2.35-2.08 (m, 4H), δ 1.62-1.61 (d, 6H), δ 0.93-0.86 (m, 2H).

MS: [M+H], 605.2.

(2) Chiral Resolution of Compound 3

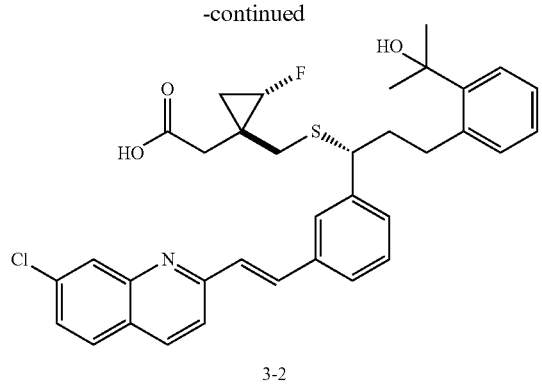

3-2

By chiral column separation, compound 3-1 (cis) and compound 3-2 (trans) could be obtained.

Compound 3-1 (cis):

$^1$H NMR (CDCl$_3$ 400 MHz): δ 8.08-8.04 (m, 2H), δ 7.75-7.47 (m, 4H), δ 7.45-7.32 (m, 6H), δ 7.17-7.11 (m, 3H), δ 4.84 (br, 1H) δ 4.52-4.27 (m, 1H), δ 4.01-3.93 (m, 1H), δ 3.19-3.14 (m, 1H), δ 2.93-2.52 (m, 4H), δ 2.38-2.18 (m, 4H), δ 1.61-1.60 (d, 6H), δ 0.98-0.76 (m, 2H).

$^{19}$F NMR (CDCl$_3$ 470 MHz): δ −216.

Compound 3-2 (trans):

$^1$H NMR (CDCl$_3$ 400 MHz): $^1$H NMR (CDCl$_3$ 400 MHz): δ 8.07-8.04 (m, 2H), δ 7.76-7.47 (m, 4H), δ 7.45-7.33 (m, 6H), δ 7.17-7.10 (m, 3H), δ 4.63 (br, 1H), δ 4.74-4.36 (m, 1H), δ 4.07-3.99 (m, 1H), δ 3.24-3.13 (m, 1H), δ 2.94-2.53 (m, 4H), δ 2.39-2.18 (m, 4H), δ 1.62-1.60 (d, 6H), δ 0.93-0.81 (m, 2H).

$^{19}$F NMR (CDCl$_3$ 470 MHz): δ −217.

(3) Synthesis of Compound 4

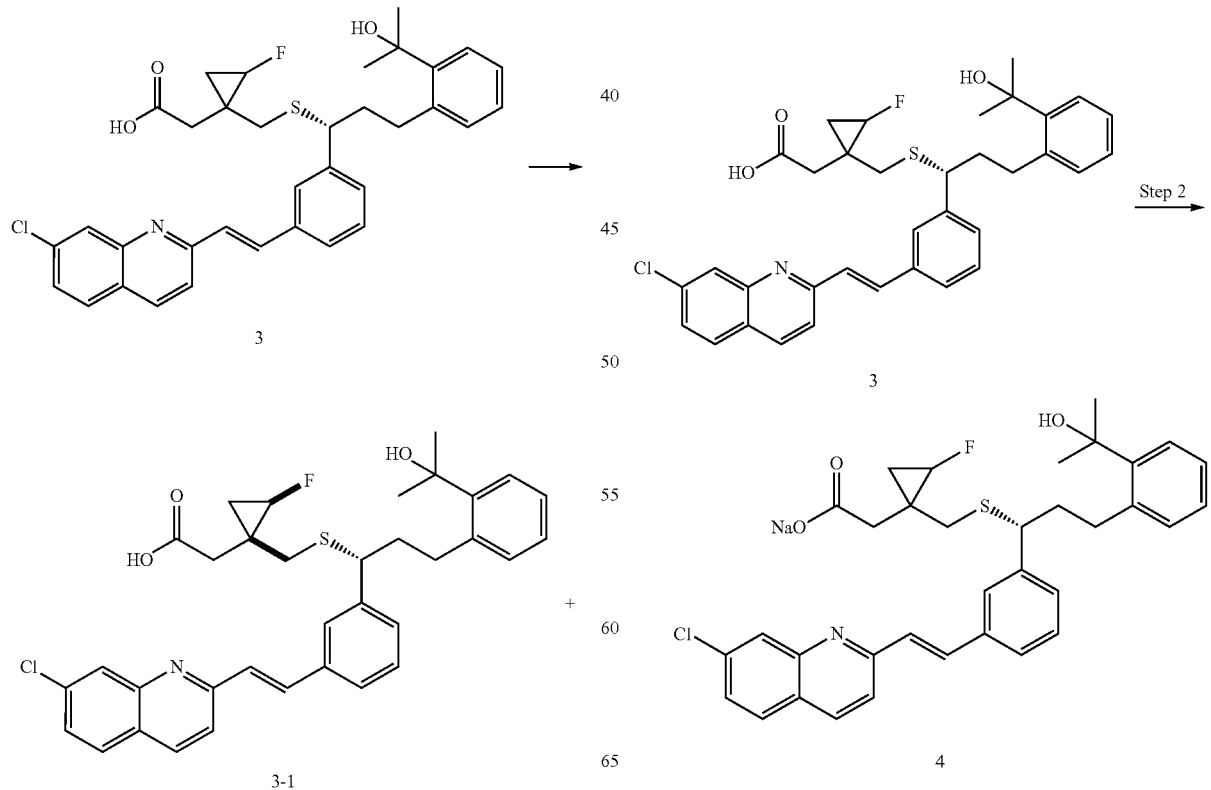

At room temperature, NaOH (8.7 mol) was firstly dissolved in methanol (30 mL), then the alkaline liquor was added into the solution of the compound 3 (8.5 mol) in methanol (32 mL), stirred for 30 min, and then added with a suitable amount of activated carbon, stirred for 30 min, and filtered by paving Celite, then the filtrate was dried by rotary evaporation, and dried under vacuum to obtain compound 4 (yield: 90%).

¹H NMR (CDC₃ 400 MHz): δ 8.03-8.00 (m, 2H), δ 7.67-7.55 (m, 4H), δ 7.43-7.33 (m, 6H), δ 7.09-7.02 (m, 3H), δ 4.58-4.31 (m, 1H), δ 4.00-3.93 (m, 1H), δ 3.28-3.16 (m, 1H), δ 2.86-2.53 (m, 4H), δ 2.23-2.09 (m, 4H), δ 1.59-1.55 (d, 6H), δ 0.70-0.53 (m, 2H).

MS: [M+H], 605.2.

(2) Chiral Resolution of Compound 4

The compound 4 was separated through a chiral column to obtain four compounds with different absolute configurations, which were illustrated as follows:

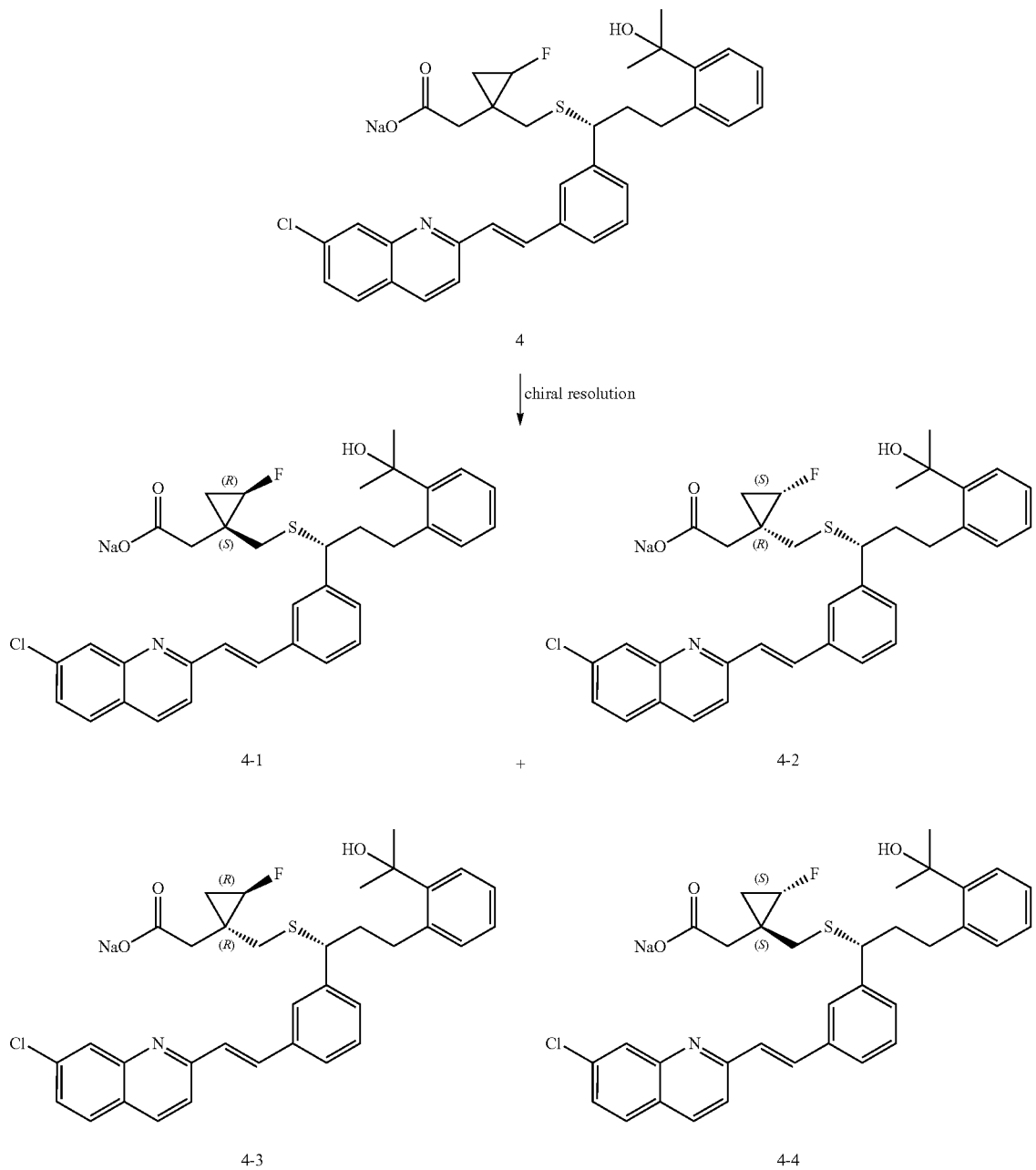

By chiral column separation, a pair of enantiomers of the cis compound were obtained, which were 2.4 g compound 4-1 and 2.2 g compound 4-2 respectively.

Compound 4-1 (CS-0090-1):
LC-MS: 4.758 min, 96.7%; [M+H], 605.2.
SFC: 4.56 min, de value: 97.79%.
Compound 4-2 (CS-0090-2):
LC-MS: 4.758 min, 99.1%; [M+H], 605.2.

SFC: 6.36 min, de value: 100%.

$^1$H NMR (CDCl$_3$ 400 MHz): δ 8.06-8.04 (m, 2H), δ 7.69-7.57 (m, 4H), δ 7.46-7.33 (m, 6H), δ 7.18-7.08 (m, 3H), δ 4.41-4.24 (m, 1H), δ 3.97-3.93 (m, 1H), δ 3.23-3.16 (m, 1H), δ 2.90-2.45 (m, 4H), δ 2.24-2.15 (m, 1H), δ 1.61-1.59 (d, 6H), δ 0.93-0.68 (m, 2H).

$^{13}$C NMR (CDCl$_3$ 500 MHz): δ 176.3, δ 156.8, δ148.1, δ145.2, δ 143.4, δ143.2, δ140.1, δ136.5, δ136.4, δ135.7, δ135.3, δ131.5, δ129.1, δ128.7, δ128.5, δ127.6, δ127.2, δ127.1, δ126.7, δ126.4, δ 125.7, δ125.6, δ125.4, δ119.2, δ75.4, δ73.7, δ50.3, δ 39.8, δ 36.1, δ34.5, δ32.3, δ31.8, δ 31.7, δ21.4, δ 17.8.

$^{19}$F NMR (CDC$_3$ 470 MHz): δ −215.

By chiral column separation, only 30 g racemate of the trans compound (compound 4-3 and 4-4(1:1) can not be separated by a chiral column) were obtained.

Compound 4-4 (CS-0090-4)

LC-MS: 9.322 min, 99.1%; [M+H], 605.2.

HPLC: 8.689 min, 99.1%.

$^1$H NMR (CDCl$_3$ 400 MHz): δ 8.07-8.04 (m, 2H), δ 7.76-7.55 (m, 4H), δ 7.47-7.33 (m, 6H), δ 7.17-7.10 (m, 3H), δ 4.63-4.36 (m, 1H), δ 4.06-4.01 (m, 1H), δ 3.19-3.16 (m, 1H), δ 2.91-2.37 (m, 4H), δ 2.26-2.22 (m, 4H), δ 1.62-1.57 (d, 6H), δ 0.93-0.81 (m, 2H).

$^{13}$C NMR (CDCl$_3$ 500 MHz): δ 174.7, δ 156.9, δ 147.8, δ 145.1, δ 143.6, δ 143.4, δ 140.1, δ 136.5, δ 136.3, δ 135.8, δ 135.7, δ 131.5, δ 129.1, δ 128.7, δ 128.6, δ 127.4, δ 127.7, δ 127.1, δ 126.7, δ 126.4, δ 125.6, δ 125.5, δ 125.4, δ 119.1, δ76.7, δ 73.8, δ50.5, δ 39.9, δ 38.1, δ32.8, δ32.2, δ31.8, δ31.6, δ21.9, δ 18.4.

$^{19}$F NMR(CDCl$_3$ 470 MHz): δ −216.

Test Parts:

Anti-Asthmatic Pharmacodynamics Experiment of Leukotriene Receptor Antagonist CS-0090 Series Compounds Part One: Acute Toxicity Experiment in Mice 1 Instruments and Materials 1.1 Experimental Animals 1.1.1 Strain and level: KM mice, ordinary level.

1.1.2 Number and sex: 40, half male and half female.

1.1.3 Weight: the mice were 18 to 22 g at purchase.

1.1.4 Supply Organization: provided by Laboratory Animal Center of Guangzhou University of Chinese Medicine.

1.1.5 Recognition method: hair staining method was adopted. The mice were numbered by saturated picric acid, and the hair on different parts of the mouse body surface was spotted to represent different numbers. The mice were marked and recognized by both numbers of the mouse skin staining and cages.

1.1.6 Breeding and management: the animals were raised in a conventional animal room, and the experimental animal license number was: SCXK (Guangdong) 2013-0020. Animal breeding condition: 10 mice/cage and group breeding, breeding temperature and humidity: 20 to 25° C., 40 to 70%; With 10 h:14 h day and night intermittent lighting, the animals were freely access to food and water during the experiment. Conditions in the breeding room were kept stable all the time to ensure the reliability of the experimental results.

1.1.7 Quarantine: the mice purchased were quarantined for seven days. During this period, the animals were checked once a day. If any unhealthy animal was found, eliminated immediately, and healthy animals were selected for the experiment.

1.2 Main Reagents anhydrousethanol (Tianjin Damao Chemical Reagent Factory), Tween-80 (Jiangsu Hai'an Petroleum Chemical Factory), deionized water (Laboratory-prepared by the College of Pharmacy of Guangdong Pharmaceutical University (广东药学院药科 学院实验室自制)), picric acid (Beijing Xinding Pengfei Science and Technology Development Co., Ltd. (北京鑫鼎鹏飞科 技发展有限公司)), formaldehyde solution (Tianjin Damao Chemical Reagent Factory), physiological saline (Laboratory-prepared by the College of Pharmacy of Guangdong Pharmaceutical University), Montelukast (ChemStone (Guangzhou) Co., Ltd. (广州康瑞泰药 业有限公司)), CS-0090-1, CS-0090-2 and CS-0090-4 (provided by ChemStone (Guangzhou) Co., Ltd., Lot No.: 20141012).

1.3 Main Instruments and Materials 0.01 mg electronic balance (Shimadzu, Japan, Product No: AUW120D), electronic balance (Shimadzu, Japan, Product No: AUY120), V7 fast mixer (Essenscien, US), electrothermal thermostatic water tank (Shanghai Yiheng Instruments Co., Ltd. (上海一恒科技有限公司), Product No: DK-8D), and 1 mL disposable sterile injector (Becton, Dickinson and Company, US).

2 Experimental Method 2.1 Dose Design and Grouping 2.1.1 Dose Design 2.1.1.1 Montelukast: a recommended intake dosage of montelukast for human is 10 mg/d (calculated by a standard human body weight of 60 kg), thereby an equivalent dosage of the mice is 1.52 mg·kg$^{-1}$·d$^{-1}$, and the administration dosage is 1500 times of the equivalent dosage, which is 2280·kg$^{-1}$·d$^{-1}$. The specific dosing regimen was: 760 mg·kg$^{-1}$, 0.01 ml/g, and three times a day.

2.1.1.2 CS-0090-1, CS-0090-2 and CS-0090-4: to facilitate the results comparison, the dosing regimens of CS-0090-1, CS-0090-2 and CS-0090-4 were set to be the same as montelukast.

2.1.2 Animal Grouping

The animals were randomly divided into four groups by weights after the adaption period, i.e. a positive drug male control group, a positive drug female control group, a CS-0090-1 male experimental group and a CS-0090-1 female experimental group, and 10 mice in each group.

2.2 Acute Toxicity Effects of CS-0090-1, CS-0090-2 and CS-0090-4 in KM Mice 2.2.1 Drug Formulation Method 2.2.1.1 Montelukast: a certain amount of montelukast was weighed, an appropriate amount of Tween-80 was added to obtain a concentration of 0.2% thereof and an appropriate amount of ethanol was added to obtain a concentration of 10% thereof, and then the mixture was vortexed and completely dissolved, then an appropriate amount of deionized water was added to formulate a ready-to-use medical liquid having a concentration of 76 mg/mL.

2.2.1.2 CS-0090-1, CS-0090-2 and CS-0090-4: a certain amount of CS-0090-1, CS-0090-2 and CS-0090-4 were weighed, an appropriate amount of Tween-80 was added to obtain a concentration of 0.2% thereof and an appropriate amount of anhydrous ethanol was added to obtain a concentration of 10% thereof, and then the mixture was vortexed and completely dissolved, then an appropriate amount of deionized water was added to formulate a ready-to-use medical liquid having a concentration of 76 mg/mL.

2.2.2 Test Procedures

The animals were randomly divided into four groups by body weight after finishing the adaption period, i.e. a positive drug male control group, a positive drug female control group, a test reagent male experimental group and a test reagent female experimental group, and 10 mice/group. The mice in each group were fasted for 12 hours before administration with water ad libitum. The animals in each group were administered corresponding therapy drugs of 0.01 ml/g of their body weight by oral gavage, three times/day, and totally administered for one day. On Day 8, the mice were dissected with their lungs and bronchi taken to be fixed and saved in a formaldehyde solution.

2.2.3 Detection Indicators 2.2.3.1 Daily observation: in the first 30 min after administration, each animal should be observed at least once; in the following 24 h after administration, the animals should be observed regularly (time interval of the observation was determined by the toxic reaction, time of onset and time of recovery cycle, and particular attention should be paid within 4 h after administration); hereinafter, the animals were observed once a day, and were totally observed for 7 days. The administration procedure and the signs of toxicity and death of the animals within the observation period were observed and recorded.

2.2.3.2 Observation of persistent toxic symptom: Additional observations will be necessary if the animals continue to display signs of toxicity. The observations should include changes in skin and fur, eyes and mucous membranes, respiratory, circulatory, autonomic nucleuses and central nervous systems, somatomotor activities and behavioral patterns. Attentions should be directed to observations of tremors, convulsions, salivation, diarrhea, lethargy and coma. Observation items for the toxic manifestions of rodent animals were showed in Table 1.

CS-0090-4; From a preliminary experiment, it is known that the mice in the experimental group were not 100% dead when administrated a dosage of 500 times (760 mg·kg$^{-1}$) of the initial dosage by intragastric administration. As the CS-0090-1, CS-0090-2 and CS-0090-4 have a very low solubility in water, the dosage form can only be suspension; if increasing the drug concentration further, it is difficult to form a more stable system with the drug and solvents, which may lead inaccurate intragastric administration dosage, which means that the LD50 of the CS-0090-1, CS-0090-2 and CS-0090-4 cannot be determined; therefore, only the maximum drug dosage of the CS-0090-1, CS-0090-2 and CS-0090-4 in the mice can be determined.

Acute toxicity effect tests of montelukast (which was provided by Chem-Stone (Guangzhou) Co., Ltd.) in KM mice showed that none of the mice died except one of the positive drug female group died in the next day and these mice were normal in ingestion, activity behavior, urine and defecation, and had no special secretions, no toxic reactions of nervous system, such as reduced activity, keeping still and less movement, alarmed drunk-like walking and other symptoms; on Day 8, an anatomical observation was performed on the mice and found that both the lungs and bronchi of the

TABLE 1

Observation Items for the Toxic Manifestions of Rodent Animals

| Organ system | Observation and inspection item | General toxic manifestions |
| --- | --- | --- |
| Central nervous system and somatic movement | Behavior | Postures changed, abnormal sound, disturbed or dull |
| | Action | Tremor, ataxy, paralysis, eclampsia, forced action |
| | Reaction on various stimulations | Excitable, hypergnosia, or lack of perception |
| | Cerebral and spinal reflex | Weakened or disappeared |
| | Muscle tone | Tetanic, and tardive |
| Autonomic nerves system | Pupil size | miosis or mydriasis |
| | Secretion | Salivation, lacrimation |
| Respiration property | Nostril | nasal discharge |
| | Respiration property and rate | Bradypnoea, breathing difficult, and cheyne-stokes respiration |
| Cardiovascular system | Cardiac palpation | Bradyrhythmia, anisorhythmia, too strong or too weak heartbeat |
| Gastrointestinal system | Belly shape | Flatuous or contracted, diarrheal or belly-bound |
| | Feces hardness and color | Unshapen feces in black or grey |
| Genitourinary system | Vulvae, mammary gland | Swelled |
| | Priapus | Prolapsed |
| | Perineum | Squalid |
| Skin and fur | Color, and tension | red, corrugated, relaxed, tetter |
| | Integrity | Piloerection |
| Mucous membranes | Mucous membranes | Mucus discharged, hyperemia, hemorrhagic cyanosis cyanosis, and pallored |
| | Oral cavity | Ulcerous |
| Eyes | Palpebra | Upper eyelid cambered |
| | Eyebulb | Ophthalmoptosis or nystagmus |
| | Transparency | Dimness |
| Others | Cecum or skin temperature | Reduced or increased |
| | General situations | Abnormal postures, and wizened |

2.2.3.3 Dissection: The animals died within the observation period were subjected to necropsy; At the end of the observation period, the surviving mice were sacrificed by cervical dislocation for necropsy. The pathological changes of lung and bronchus of each animal were recorded, and histopathological examination was conducted on the observed visceral organs.

3 Results

The dosage of the mice was converted and obtained according to a recommended dosage (10 mg/d) of a positive drug montelukast for human, and used as an initial dosage (1.52 mg·kg$^{-1}$) of the test drugs CS-0090-1, CS-0090-2 and mice were normal. In view of individual differences, the maximum dosage of montelukast can be deemed as 760 mg·kg$^{-1}$*3=2280 mg·kg$^{-1}$.

Acute toxicity effect tests of CS-0090-1, CS-0090-2 and CS-0090-4 (which were provided by Chem-Stone (Guangzhou) Co., Ltd.) in KM mice showed that none of the mice died, and these mice were normal in ingestion, activity behavior, urine and defecation, and had no special secretions, no toxic reactions of nervous system, such as reduced activity, keeping still and less movement, alarmed drunk-like walking and other symptoms; on Day 8, an anatomical observation was performed on the mice and found that both the lungs and bronchi of the mice were normal. Therefore, the maximum dosages of the CS-0090-1, CS-0090-2 and CS-0090-4 can also be deemed as 760 mg·kg$^{-1}$*3=2280 mg·kg$^{-1}$, 763 mg·kg$^{-1}$*3=2289 mg·kg$^{-1}$, 754 mg·kg$^{-1}$*3=2262 mg·kg$^{-1}$, respectively, which demonstrated that the CS-0090-1, CS-0090-2 and CS-0090-4 were relatively safe, reliable and innoxious in a therapeutic dosage range.

Part Two: In-Vivo Anti-Asthmatic Pharmacodynamics Experiment of Compound CS-0090-1

1 Instruments and Materials 1.1 Experimental Animals 1.1.1 Strain and level: guinea pigs, ordinary level.

1.1.2 Numbers and sex: 24, male.

1.1.3 Weight: the guinea pigs were 180 to 220 g at purchase.

1.1.4 Supply Organization: provided by Laboratory Animal Center of Guangzhou University of Chinese Medicine.

1.1.5 Recognition method: hair staining method was adopted. The guinea pigs were numbered by saturated picric acid, and the hair on different parts of the guinea pigs body surface was spotted to represent different numbers. The guinea pigs were marked and recognized by both numbers of the guinea pigs skin staining and cages.

1.1.6 Breeding and management: the animals were raised in a conventional animal room, and the experimental animal license number was: SCXK (Guangdong) 2013-0020. Animal breeding condition: 6 guinea pigs/cage and group breeding, breeding temperature and humidity: 20 to 25° C., 40 to 70%; With 10 h:14 h day and night intermittent lighting, and the animals were freely access to food and drink water during the experiment. Conditions in the breeding room were kept stable all the time to ensure the reliability of the experimental results.

1.1.7 Quarantine: the guinea pigs purchased were quarantined for three days. During this period, the animals were checked once a day. If any unhealthy animal was found, eliminated immediately, and healthy animals were selected for the experiment.

1.2 Main Reagents acetylcholine chloride (Shanghai SSS Reagent Co., Ltd.), histamine (Beijing Lvyuan Bode Biological Technology Co., Ltd. (北京绿源博德生物科技有限公司)), anhydrous ethanol (Tianjin Damao Chemical Reagent Factory), Tween-80 (Jiangsu Hai'an Petroleum Chemical Factory), picric acid (Beijing Xinding Pengfei Science and Technology Development Co., Ltd.), deionized water (Laboratory-prepared by the College of Pharmacy of Guangdong Pharmaceutical University), Montelukast (Chem-Stone (Guangzhou) Co., Ltd.), and CS-0090-1 (Chem-Stone (Guangzhou) Co., Ltd.).

1.3 Main Instruments and Material s

V7 fast mixer (Essenscien, US), electrothermal thermostatic water tank (Shanghai Yiheng Instruments Co, Ltd., Product No: DK-8D), Yuwell 402AI ultrasonic atomizer (Jiangsu Yuyue Medical Equipment & Supply Co., Ltd.), electronic balance (Shimadzu, Japan, Product No: AUY120), 0.01 mg electronic balance (Shimadzu, Japan, Product No: AUW120D), and 1 mL disposable sterile injector (Becton, Dickinson and Company, US).

2 Experimental Method 2.1 Establishment of Guinea Pig Asthma Models

Mixing-atomization induced asthma method of 0.1% histamine and 2% acetylcholine solution was adopted. 180 to 220 g male guinea pigs were taken and placed in a lab-prepared closed container (2 L) the day before experiment, inhaling a mixed solution of 0.1% histamine and 2% acetylcholine by ultrasonic atomization, a maximum atomization volume was adjusted and pulverization was continued until the guinea pigs had signs of cough. Observing the time period from the beginning of the guinea pigs' inhalation to develop convulsions and tumble (which is the asthma-induced latent period). The guinea pigs having an asthma-induced latent period within 120 s were deemed to be qualified sensitive animals, and the qualified animals were selected for grouping and administration.

2.2 Dose Design and Grouping 2.2.1 Dose Design 2.2.1.1 Montelukast: A recommended intake dosage of montelukast for human is 10 mg/d (calculated by a standard human body weight of 60 kg), thereby an equivalent dosage of the guinea pig is 1 mg·kg−1·d−1, and the administration dosage is three times of the equivalent dosage, which is 3 mg·kg$^{-1}$·d$^{-1}$.

2.2.1.2 CS-0090-1: one times of the equivalent dosage of montelukast was used as a low dosage of CS-0090-1, i.e., 1 mg·kg$^{-1}$·d$^{-1}$; three times of the equivalent dosage of montelukast, i.e., 3 mg·kg$^{-1}$·d$^{-1}$, was used as a median dosage of CS-0090-1, and nine times of the equivalent dosage of montelukast, i.e., 9 mg·kg$^{-1}$·d$^{-1}$, was used as high dosage of the CS-0090-1.

2.2.2 Animal Grouping

The guinea pigs with qualified induced asthma latent period were randomly divided into four groups by weight, i.e., a montelukast control group, a CS-0090-1 low-dosage experimental group, a CS-0090-1 median-dosage experimental group, and a CS-0090-1 high-dosage experimental group, and six guinea pigs in each group.

2.3 Anti-Asthmatic Effect of CS-0090-1 on the Guinea Pig Asthma Models 2.3.1 Drug Formulation Method 2.3.1.1 Montelukast: a certain amount of montelukast was weighed, an appropriate amount of Tween-80 was added to obtain a concentration of 0.2% thereof and an appropriate amount of ethanol was added to obtain a concentration of 10% thereof, and then the mixture was vortexed and completely dissolved, then an appropriate amount of deionized water was added to formulate a ready-to-use medical liquid having a concentration of 0.6 mg/mL.

2.3.1.2 CS-0090-1: a certain amount of CS-0090-1 was weighed, an appropriate amount of Tween-80 was added to obtain a concentration of 0.2% thereof and an appropriate amount of ethanol was added to obtain a concentration of 10% thereof, and then the mixture was vortexed and completely dissolved, then an appropriate amount of deionized water was added to formulate a high-dosage solution having a concentration of 0.2 mg/mL. A median-dosage solution having a concentration of 0.6 mg/mL, and a low-dosage solution having a concentration of 1.8 mg/mL were fomulated by the same method, wherein the solutions were prepared ready-to-use.

2.3.1.3 A mixed solution of 0.1% histamine and 2% acetylcholine: a certain amount of histamine was weighed, and an appropriate amount of deionized water was added to formulate a histamine solution having a concentration of 0.1%; a certain amount of acetylcholine was weighed, and an appropriate amount of deionized water was added to formulate a acetylcholine solution having a concentration of 2%; then the above two solutions were mixed isometrically, wherein the solution was prepared ready-to-use.

2.3.2 Test Procedures 24 guinea pigs with qualified induced asthma latent period were randomly divided into four groups by weight, i.e., a montelukast control group, a CS-0090-1 low-dosage experimental group, a CS-0090-1 median-dosage experimental group, and a CS-0090-1 high-dosage experimental group, and six guinea pigs in each group. The guinea pigs in each group were fasted for 12 hours before administration with water ad libitum, and were administered corresponding therapy drugs of 1 ml/100 g of their body weight by oral gavage once a day, and the drug was continuously administered for seven days. After 1 h of the last administration on the seventh day, the guinea pigs were placed in a lab-prepared closed container (2 L) again to induce asthma under the same condition of preparing the asthma models, and observing and recording the induced asthma latent period after the administration of the guinea pigs, wherein the latent period exceeding 6 min were calculated as 6 min.

2.3.3 Statistical Analysis

Statistical analysis was performed in Excel. The data of all experimental results was expressed as mean±standard deviation (x±s). By using T-test, when P≤0.05, the two data sets had significant differences; and when P>0.05, the two data sets had no significant differences.

3 Results

No blank control group was designed in this experiment, and a self-control method before and after administration was adopted, wherein the numbers of the animals satisfied the statistics requirements, and each group included six guinea pigs that were successfully induced. As shown in the Table below, when comparing the induced asthma latent period of the CS-0090-1 median-dosage group after administration and the same group before administration, P<0.05, which indicated there were significant differences; the CS-0090-1 median-dosage significantly prolonged the induced asthma latent period of the guinea pig, which indicating a more noticeable effect than the montelukast control group of the same dosage; however, the P value of the CS-0090-1 low-dosage group and the CS-0090-1 high-dosage group were more than 0.05, which indicated no significant differences when compared with the induced asthma latent period of the group theirselves before administration, which means that anti-asthmatic effects of the CS-0090-1 low-dosage group and the CS-0090-1 high-dosage group were not noticeable on the guinea pig asthma models, the reason may be that the low-dosage CS-0090-1 did not reach the minimum anti-asthmatic effective dosage, thus the anti-asthmatic effect on the guinea pig asthma models was not obvious. While the the median-dosage CS-0090-1 had reached the maximum effective dosage, thus the anti-asthmatic effect on the guinea pig asthma models was not obvious when the dosage was increased continuously.

4 Brief Summary

In the in-vivo pharmacodynamics experiments, while compared with the positive control drug montelukast, both the median-dosage and high-dosage of CS-0090-1 can significantly prolong the induced asthma latent period of the guinea pigs (P values were both smaller than 0.05), which indicates that it has a favourable anti-asthmatic effect on the guinea pig asthma models, and is a candidate lead compound having a druggability prospect. Pharmaceutics studies may be performed to improve the bioavailability of CS-0090-1, which could provide more experimental basis for further druggability evaluation.

Part Three: Studies on In-Vivo Anti-Asthmatic Pharmacodynamics of Compound CS-0090-2

1 Instruments and Materials 1.1 Drugs and Reagents

Both montelukast and the tested drugs CS-0090-2 were provided by Chem-Stone (Guangzhou) Co., Ltd.; acetylcholine chloride (acetylcholine, Shanghai SSS Reagent Co., Ltd); histamine phosphate (histamine, Beijing Lvyuan Bode Biological Technology Co., Ltd.); anhydrous ethanol (Tianjin Damao Chemical Reagent Factory), Tween-80 (Jiangsu Hai'an Petroleum Chemical Factory); Sodium chloride (NaCl, Guangdong Guanghua Sci-Tech Co., Ltd); potassium chloride (KCl, Tianjin Baishi Chemical Co., Ltd.); calcium chloride ($CaCl_2$, Tianjin Zhiyuan Chemical Reagent Co., Ltd. (天津市致远化学 试剂有限公司)); sodium hydrogen carbonate ($NaHCO_3$, Tianjin Zhiyuan Chemical Reagent Co., Ltd.); potassium dihydrogen phosphate ($KH_2PO_4$, Tianjin Fuchen Chemical Reagents Factory); magnesium sulfate ($MgSO_3$, Tianjin Damao Chemical Reagent Factory); glucose (Glucose Tianjin Baishi Chemical Co., Ltd.); formaldehyde (Tianjin Damao Chemical Reagent Factory); physiological saline (Laboratory-prepared by the College of Pharmacy of Guangdong Pharmaceutical University); and picric acid (Beijing Xinding Pengfei Science and Technology Development Co., Ltd.).

1.2 Experimental Animals

Guinea pig: 180 to 220 g of body weight (induced asthma), healthy and male.

White mouse: Kunming strain, 20 to 25 g of body weight, half female and half male.

All the above animals were provided by the Lab of the College of Pharmacy of Guangdong Pharmaceutical University, and the certification number of the mice was: SCXK (Guangdong) 2013-0020; and the use license number of the guinea pigs was: SCXK (Guangdong) 2013-0020.

TABLE 2

Result of CS-0090-1 Anti-asthmatic Effect on Guinea Pig Asthma Models

| Group | Animal Number (piece) | Dosage (mg · kg$^{-1}$) | Induced asthma latent period before administration (s) | Induced asthma latent period after administration (s) |
| --- | --- | --- | --- | --- |
| Montelukast control group | 6 | 3 | 48.17 ± 4.62 | 63.00 ± 7.13* |
| CS-0090-1 low-dosage experimental group | 6 | 1 | 49.17 ± 8.70 | 60.33 ± 17.11 |
| CS-0090-1 median-dosage experimental group | 6 | 3 | 60.17 ± 9.47 | 209.83 ± 164.74*# |
| CS-0090-1 high-dosage experimental group | 6 | 9 | 63.50 ± 11.57 | 215.67 ± 78.09*# |

Note:
*compared with the induced asthma latent period of the group itself before administration, P < 0.05, there was significant difference;
compared with the induced asthma latent period of the montelukast positive control, P < 0.05, there was significant difference.

1.3 Experimental Instruments

Yuwell 402AI ultrasonic atomizer (Jiangsu Yuyue Medical Equipment & Supply Co., Ltd.); $ZC^{-1}0$ intelligent super thermostatic water tank (Ningbo Tianheng Instrument Factory); Xinhang JZ100 tonotransducer (Beijing Xinhang Xingye Technology Trade Co., Ltd.); MedLab biosignal acquisition and processing system (Nanjing Medease Science and Technology Co., Ltd.); 0.1 mg electronic balance (Shimadzu, Japan, Product No.: AUY120); 0.01 mg electronic balance (Shimadzu, Japan, Product No.: AUW120D); electrothermal thermostatic water tank (Shanghai Yiheng Instruments Co., Ltd., DK-8D); BIOLAB swirl blender MB (Shanghai BIOLAB Equipment Co., Ltd.); and ultrasonic cleaner (Dongguan Keqiao Ultrasonics Facilities Co., Ltd. ( 东莞市科桥超声 设备有限公司 )).

2 Experimental Method 2.1 Establishment of Histamine and Acetylcholine Induced Asthma Animal Models of Guinea Pigs 2.1.1 Dosage Setting The clinic dosage of montelukast was 10 mg/d, and administered once a day. A standard human body weight was set as 60 kg, then the clinic dosage was 0.17 mg·kg$^{-1}$. According to a equivalent dosage ratio calculated by the body surface area of human and the guinea pig, the dosage of the guinea pig was set as 3 mg·kg$^{-1}$. Similar to the above description, to facilitate to compare the medical effects, a high, median and low dosage of the tested drug CS-0090-2 were 9 mg·kg$^{-1}$, 3 mg·kg$^{-1}$ and 1 mg·kg$^{-1}$ respectively.

2.1.2 Model Preparation and Dosing Scheme 180 to 220 g health guinea pigs were taken, and placed in a closed glass bell jar one by one firstly; after the guinea pigs became quiet, an atomization apparatus was started to spray an asthma-induced medical liquid (a solution of 2% acetylcholine chloride and 0.1% histamine phosphate mixed in equal volume) for 15 s, then the pulverization was stopped, and the asthma latent period (time period from the beginning of pulverization to onset of asthma and dyspnea, till convulsions and tumble) was observed, and qualified animals having a asthma latent period ≤120 s were screened. The qualified guinea pigs screened were randomly divided into four groups, which were a high-dosage group, a median-dosage group, a low-dosage group, and a positive control group respectively.

On the next day, 42 qualified guinea pigs were selected, randomly divided into four groups with 6 guinea pigs in each group, which were 3 mg·kg$^{-1}$ of montelukast group, and 1, 3 and 9 mg·kg$^{-1}$ of the tested drug CS-0090-2 groups. The guinea pigs in each group were subjected to oral gavage administration continuously for 7 days with a dosage of 1 ml/100 g. The guinea pigs were placed in the closed glass bell jar one by one in 1 h after the administration on the last day, and pulverization was performed for inducing asthma under the same experimental conditions to the screen experiment. The asthma latent period and the number of the convulsions animals were recorded, wherein the animals did not tumble beyond 360 s were calculated as 360 s.

2.2 Statistical Test

Experimental data was represented by ±s, and data statistics was processed by SPSS11.0.

The asthma latent period was prolonged significantly (P<0.05). After the CS-0090-2 (1, 3 and 9 mg·kg$^{-1}$) was administered for seven days, the asthma latent period of the guinea pig was not changed apparently through self-control before and after administration.

TABLE 3

Anti-asthmatic Effect of CS-0090-2 on Histamine and Acetylcholine Induced Asthma Guinea Pigs ($\bar{x} \pm s$)

| Group | Animal Number (piece) | Dosage (mg · kg$^{-1}$) | Induced asthma latent period (s) within 6 min | |
|---|---|---|---|---|
| | | | Before administration | After administration |
| Montelukast | 6 | 3 | 48.2 ± 4.6 | 59.8 ± 7.1* |
| CS-0090-2 low-dosage | 6 | 1 | 47.8 ± 7.6 | 126.3 ± 155.9 |
| CS-0090-2 median-dosage | 6 | 3 | 54.8 ± 7.5 | 132.3 ± 151.9 |
| CS-0090-2 high-dosage | 6 | 9 | 60.7 ± 10.1 | 57.0 ± 6.1 |

Note:
compared with the situation before administration:
*P < 0.05;
**P < 0.01.

4 Brief Summary

In the induced asthma experiment of guinea pigs, the novel compound CS-0090-2 had no antagonism effects on the asthma of the guinea pigs.

Part Four: Studies on In-Vivo Anti-Asthmatic Pharmacodynamics of Compound CS-0090-4

1 Instruments and Materials 1.1 Experimental Animals

Healthy and male guinea pigs with a body weight of 180 to 220 g (provided by the Laboratory Animal Center of Guangdong Pharmaceutical University, and the certification number was SCXK (Guangdong) 2013-0020).

1.2 Main Instruments 0.01 mg electronic balance (Shimadzu, Japan, Product No.: AUY120), electronic balance (Shimadzu, Japan, Product No.: AUY120), V7 fast mixer (Essenscien, US), Yuwell 402AI ultrasonic atomizer (Jiangsu Yuyue Medical Equipment & Supply Co., Ltd.); and electronic balance (SHIMADZU/Shimadzu, Product No.: AUW120D)

1.3 Main Reagents and Materials acetylcholine chloride (Shanghai SSS Reagent Co., Ltd., lot number: 20021018), histamine phosphate (Shanghai Lizhu Dongfang Biotechnics Co., Ltd. (上海丽珠东方生 物技术有限公司), lot number: 010310), montelukast (provided by Chem-Stone (Guangzhou) Co., Ltd.), and CS-0090-4 (provided by Chem-Stone (Guangzhou) Co., Ltd.).

2 Experimental Method 2.1 Formulation of Asthma-Induced Solution 0.2 g choline and 0.01 g histamine were weighed and put into beakers respectively, and then respectively each beaker were added with 10 ml distilled water and blended to homogeneity.

2.2 Influences of CS-0090-4 on the Asthma Latent Period of Guinea Pigs 2.2.1 Establishment of Induced Asthma Animal Models of Guinea Pigs The purchased guinea pigs were quarantined for 3 days. During this period, the animals were checked once a day, any unhealthy animal found should be eliminated immediately, and healthy animals were selected for the experiment. The healthy guinea pigs with body weight of 180 to 220 g were taken and placed in a closed glass bell jar one by one firstly; after the guinea pigs became quiet, an atomization apparatus was started to spray an asthma-induced medical liquid (a solution of 2% acetylcholine chloride and 0.1% histamine phosphate mixed in equal volume) until the guinea pigs tumbled, then the pulverization was stopped, and the asthma latent period (time period from the beginning of pulverization to onset of asthma and dyspnea, till convulsions and tumble) was observed, and qualified animals having a asthma latent period ≤120 s were screened.

2.2.2 Dosage Settings

Literatures reported that a recommended intake dosage of montelukast for a human body is 10 mg/d (calculated by a standard human body weight of 60 kg), and a daily dosage was 0.17 mg·kg$^{-1}$. According to a multiple profile to convert the adult dosage into an animal dosage, it could be known that the CS-0090-4 dosages of the guinea pigs were low-dosage (1 mg·kg$^{-1}$), median-dosage (3 mg·kg$^{-1}$) and high-dosage (9 mg·kg$^{-1}$), and the dosage of montelukast of the positive control group was median-dosage (3 mg·kg$^{-1}$).

2.2.3 Dosing Scheme

The qualified guinea pigs screened were randomly divided into four groups, which were a high-dosage group, a median-dosage group, a low-dosage group, and a positive control group. The guinea pigs in each group were subjected to oral gavage administration continuously for 7 days with a dosage of 1 ml/100 g. The induced asthma latent period was determined in 1 h after administration on the last day.

3 Results 3.1 Influences of CS-0090-4 on the Asthma Latent Period of Guinea Pigs The histamine and the acetylcholine inhaled in by the guinea pigs were acted on H1 and M receptors of airway epithelial cells of the guinea pigs, which made the smooth muscle of the airway contracted, and made the guinea pigs difficult to breathe, wherein this model could simulate the airway obstruction symptom when the asthma attacks. From Table 4, it can be seen that significant differences (P<0.05) present between the latent periods before and after the administration of the 9 mg·kg$^{-1}$ group in the CS-0090-4 dosage groups, and there were no significant differences (P>0.05) between the latent periods before and after the administration of the 1 mg·kg$^{-1}$ group and the 3 mg·kg$^{-1}$ group in the CS-0090-4 dosage groups, which indicated that CS-0090-4 can remarkably prolong the asthma latent period with the dosage of 9 mg·kg$^{-1}$, while the asthma latent period can not be remarkably prolonged with the dosages of 1 mg·kg$^{-1}$ and 3 mg·kg$^{-1}$.

3.2 Influences of Montelukast on the Asthma Latent Period of Guinea Pigs

From Table 3, it can be seen that there were significant differences (P<0.05) between the latent periods before and after the administration of the 3 mg·kg$^{-1}$ of montelukast, which indicated that the asthma latent period can be remarkably prolonged with the dosage of 3 mg·kg–1 of montelukast.

TABLE 4

Anti-asthmatic Effect of CS-0090-4 on Histamine and Acetylcholine Induced Asthma Guinea Pigs ($\bar{x} \pm s$)

| Group | Dosage (mg · kg$^{-1}$) | Asthma latent period before administration | Asthma latent period after administration |
|---|---|---|---|
| Montelukast | 3 | 48.17 ± 4.62* | 59.83 ± 7.08 |
|  | 1 | 49.67 ± 9.27 | 52.83 ± 2.93 |
| CS-0090-4 | 3 | 59.50 ± 15.62 | 60.17 ± 7.33 |
|  | 9 | 45.17 ± 4.49* | 53.33 ± 6.38 |

Compared with the induced asthma latent period before administration, *P < 0.05.

4. Brief Summary

In the in-vivo anti-asthmatic experiment of guinea pigs, the CS-0090-4 had significant anti-asthmatic effect on the acetylcholine-histamine induced guinea pig asthma with a dosage of 9 mg·kg$^{-1}$, which can remarkably prolong the asthma latent period of the guinea pigs, while the montelukast had significant anti-asthmatic effect (P<0.05) on the acetylcholine-histamine induced guinea pig asthma with a dosage of 3 mg·kg$^{-1}$. Accordingly, the anti-asthmatic effect of CS-0090-4 is less marked than montelukast.

CONCLUSIONS

1. The acute toxicity tests results indicated that: the acute toxical effect experiment of the CS-0090-1, CS-0090-2 and CS-0090-4 (which were provided by Chem-Stone (Guangzhou) Co., Ltd.) on KM mice showed that none of the mice died, and these mice were normal in ingestion, activity behavior, urine and defecation, and had no special secretions, no toxic reactions of the nervous system, such as reduced activity, keeping still and less movement, alarmed drunk-like walking and other symptoms; on Day 8, an anatomical observation was performed on the mice and found that both the lungs and bronchi of the mice were normal. Therefore, the maximum dosages of the CS-0090-1, the CS-0090-2 and the CS-0090-4 can also be deemed as 2280 mg·kg$^{-1}$, 2289 mg·kg$^{-1}$ and 2262 mg·kg$^{-1}$ respectively, which demonstrates that the CS-0090-1, the CS-0090-2 and the CS-0090-4 are relatively safe, reliable and innoxious in a therapeutic dosage range.

2. The in-vivo anti-asthmatic pharmacodynamics tests results of CS-0090-1 showed that: the high-dosage CS-0090-1 significantly prolonged the induced asthma latent period of the guinea pigs, which indicates that it has good anti-asthmatic effect on the guinea pig asthma models and its effect is more significant than the montelukast control group with the same dosage (P<0.05), and is a very promising candidate lead compound for developing highly-effective low-toxicity anti-asthmatic drugs. Based on this, pharmaceutics studies may be performed to improve the bioavailability of CS-0090-1, which could provide more experimental basis for further druggability evaluation.

3. The in-vivo anti-asthmatic pharmacodynamics tests results of CS-0090-2 showed that: the compound CS-0090-2 had no antagonism effect on the asthma of the guinea pigs.

4. The in-vivo anti-asthmatic pharmacodynamics tests results of CS-0090-4 showed that: in the in-vivo anti-asthmatic experiment of guinea pigs, the CS-0090-4 had significant anti-asthmatic effect on the acetylcholine-histamine induced guinea pig asthma under a high dosage (9 mg·kg$^{-1}$) administration condition, which could remarkably prolong the asthma latent period of the guinea pigs. While the montelukast had a significant anti-asthmatic effect on the acetylcholine-histamine induced guinea pig asthma under a dosage of 3 mg·kg$^{-1}$, which could remarkably prolong the asthma latent period of the guinea pigs. Accordingly, the asthma treatment effect of the CS-0090-4 was lower than the positive control drug with respect to the positive control drug montelukast.

The invention claimed is:

1. A cyclopropyl unsaturated quinoline compound or a pharmaceutically acceptable salt thereof used as leukotriene receptor antagonist, having the structural formula as follows:

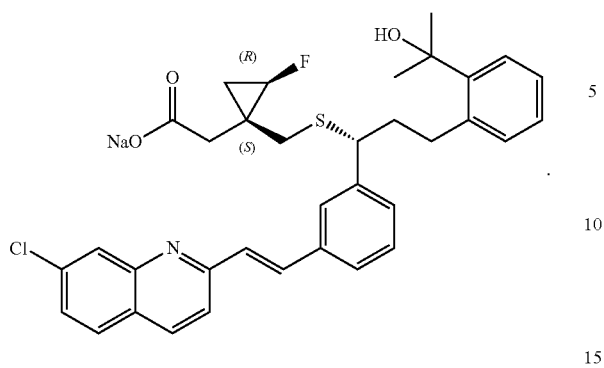
2. A pharmaceutical composition comprising an effective amount of the cyclopropyl unsaturated quinoline compound or a pharmaceutically acceptable salt thereof used as leukotriene receptor antagonist according to claim 1.
3. The pharmaceutical composition according to claim 2 further comprising a pharmaceutically acceptable excipient(s).
* * * * *